United States Patent [19]

Carleton

[11] 4,207,265
[45] Jun. 10, 1980

[54] PROCESS FOR PREPARING HYDROQUINONE AND ACETONE

[75] Inventor: Peter S. Carleton, Branford, Conn.

[73] Assignee: The UpJohn Company, Kalamazoo, Mich.

[21] Appl. No.: 563,464

[22] Filed: Mar. 31, 1975

Related U.S. Application Data

[63] Continuation of Ser. No. 388,443, Aug. 15, 1973, abandoned, which is a continuation of Ser. No. 134,871, Apr. 16, 1971, abandoned.

[51] Int. Cl.$^2$ .................. C07C 37/08; C07C 45/00
[52] U.S. Cl. ................................ 568/385; 568/768; 568/716; 568/781
[58] Field of Search ........... 260/621 R, 593 R, 621 C, 260/593 A; 568/768, 716, 781

[56] References Cited

U.S. PATENT DOCUMENTS

| | | | |
|---|---|---|---|
| 2,497,503 | 2/1950 | Jones | 260/621 |
| 2,644,014 | 6/1953 | Saunders | 260/621 |

*Primary Examiner*—Norman Morgenstern
*Assistant Examiner*—James H. Reamer
*Attorney, Agent, or Firm*—Denis A. Firth; John Kekich

[57] ABSTRACT

A process is provided for the preparation of hydroquinone by oxidizing a phenol having in the paraposition a 1-cycloalkenyl or α-methylene-(alkyl or aralkyl) group. The oxidation is carried out using hydrogen peroxide or a hydrocarbyl peroxide in the presence of an inert solvent and a catalytic amount of a strong acid which is not oxidized by the peroxide. The other product of the reaction is the ketone derived by oxidation of the para-substituent in the starting phenol, e.g. p-isopropenylphenol gives hydroquinone and acetone. The reaction forms a particularly convenient route for conversion of phenol to hydroquinone in that phenol is condensed with acetone to bisphenol A, the latter is degraded by alkaline hydrolysis to a mixture of phenol and p-isopropenylphenol, which latter is subjected, without separation, to the above process to give a mixture of hydroquinone, phenol, and acetone. The acetone and phenol are recovered and used in the preparation of bisphenol A thereby starting a new cycle of conversion.

7 Claims, No Drawings

PROCESS FOR PREPARING HYDROQUINONE AND ACETONE

This is a continuation of application Ser. No. 388,443, filed Aug. 15, 1973, now abandoned which latter is a continuation of application Ser. No. 134,871, filed Apr. 16, 1971, now abandoned.

BACKGROUND OF THE INVENTION

1. Field of the Invention

This invention relates to a process for the preparation of hydroquinone and is more particularly concerned with a process for the oxidation of p-substituted phenols to hydroquinone and with processes for the conversion of phenol to hydroquinone which incorporate this oxidation as a step therein.

2. Description of the Prior Art

Hydroquinone, and its preparation by a wide variety of methods, are well known in the art. The principal methods which have received commercial attention include (i) the reduction of quinone (obtained either by oxidation of aniline or the electrolytic oxidation of benzene); (ii) the hydrolysis of p-halogenated phenols; (iii) hydroperoxidation of p-dialkylbenzenes followed by acid hydrolysis; and (iv) the oxidation of esters of 4-(α,α-dialkylmethyl)phenols followed by acid cleavage of the resulting hydroperoxides. Illustrative of the latter method is the oxidation of the acetate of p-isopropylphenol to the corresponding hydroperoxide followed by acid cleavage of the latter to give a mixture of hydroquinone and acetone: see U.S. Pat. No. 3,028,410.

I have now found that p-isopropenylphenol and related phenols having in the para-position a 1-cycloalkenyl or an α-methylene-(alkyl or aralkyl) group can be readily converted to a mixture of hydroquinone and the appropriate ketone in high yield and in a one step reaction. I have found further that this process of my invention is particularly useful in a cyclic process in which phenol is condensed with acetone to yield bisphenol A, the bisphenol A is subjected to alkaline hydrolysis to yield a mixture of phenol and p-isopropenylphenol, the latter is subjected to the process of the invention to obtain hydroquinone and acetone, and the acetone and phenol regenerated in the various stages of the process are re-used in a further cycle of operations.

SUMMARY OF THE INVENTION

The invention, in its broadest aspect, comprises a process for the preparation of hydroquinone with process comprises reacting (i) a phenol of the formula:

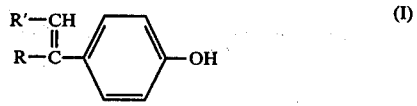

wherein R taken alone is selected from the group consisting of hydrogen, lower-alkyl and aryl, R' taken alone represents hydrogen, and R and R' taken together with the carbon atoms to which they are attached represent 1-cycloalkenyl from 5 to 7 carbon atoms, inclusive, and (ii) a peroxide selected from the group consisting of hydrogen peroxide and a hydrocarbyl peroxide in the presence of an inert solvent and a catalytic amount of a strong acid which is not oxidized by said peroxide, whereby there is obtained hydroquinone and the corresponding ketone of the formula: R—CO—CH₂—R', wherein R and R' have the significance above defined.

The invention also comprises a semi-continuous process for the conversion of phenol to hydroquinone which comprises condensing phenol with a ketone R—CO—CH₂—R', wherein R and R' are as hereinbefore defined, under known conditions to obtain the corresponding bisphenol of the formula:

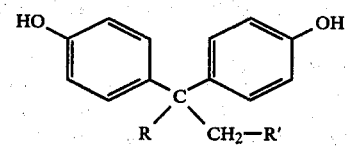

subjecting the latter to alkaline hydrolysis under known conditions to obtain a mixture of phenol and the para-substituted phenol (I), and subjecting the latter to the process of the invention to obtain a mixture of hydroquinone and ketone R—CO—CH₂—R'. The ketone obtained in the third stage of the process and the phenol recovered in the second stage are then recycled. The overall result of one cycle of this process is the net consumption of 1 mole of phenol and the production of 1 mole of hydroquinone.

The hydroquinone produced in accordance with the process of the invention is useful for all purposes for which hydroquinone is conventionally used, namely, principally as a photographic developer and as antioxidant for a wide variety of purposes particularly in the stabilization of foodstuffs and other biological materials, as well as for a diversity of more limited uses known in the art.

DETAILED DESCRIPTION OF THE INVENTION

The process of the invention can be represented schematically using the following equations:

(i) In the case where the peroxide employed is hydrogen peroxide the process is represented as follows:

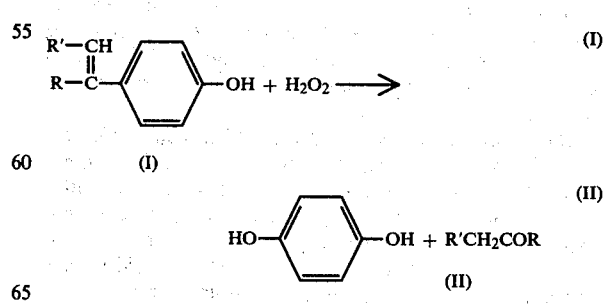

(ii) In the case where a hydrocarbyl peroxide is employed the process is represented as follows:

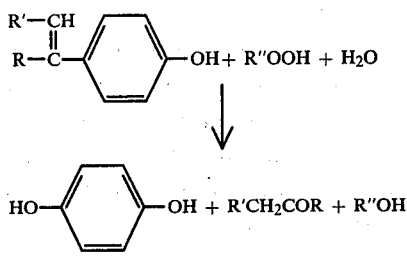

wherein R" represents hydrocarbyl as hereinafter defined.

In carrying out the process of the invention, the starting phenol (I) is dissolved or suspended in the inert solvent, the ratio of phenol (I) to solvent being not critical. Advantageously, however, the phenol (I) is present in an amount corresponding to about 10 to about 25 percent by weight in the inert solvent. The latter can be any solvent which is inert under the conditions of the reaction, i.e. does not enter into reaction with any of the reactants or interfere in any way with the desired course of the reaction. Illustrative of inert solvents are water, diethyl ether, tetrahydrofuran, dioxan, carbon disulfide, benzene, toluene, xylene, glacial acetic acid and the like.

The solution or suspension of phenol (I) in inert solvent is admixed with the peroxide. The order in which the two reactants are added one to the other is not critical. However, it is preferred that the peroxide be added to the phenol (I) and not vice versa particularly where the peroxide employed is hydrogen peroxide. Where the peroxide employed is hydrogen peroxide there can be used any of the commercially available forms containing from about 3 percent by weight to about 90 percent by weight of hydrogen peroxide in aqueous solution. Preferably, the hydrogen peroxide is employed as an aqueous solution containing about 30 percent by weight of hydrogen peroxide. Where the peroxide employed in the process of the invention is a hydrocarbyl hydroperoxide, the latter can be used in the pure state or in the form of the crude reaction mixture obtained by peroxidation of the corresponding hydrocarbon as discussed hereinafter.

The proportion of peroxide employed in the reaction mixture is advantageously at least equimolar with respect to the starting phenol (I) and preferably is in excess of the equimolar proportion and is from about 1.0 mole to about 1.5 moles per mole of starting phenol (I).

The admixture of starting phenol (I) and peroxide is advantageously carried out at ambient temperatures, i.e. of the order of about 20° C. The resulting mixture is then preferably, but not necessarily, cooled to a temperature of the order of 5° C. to about 25° C. before being treated carefully with a catalytic amount of a strong acid which is not itself susceptible to oxidation by the peroxide.

By "strong acid" is meant an acid having a pK less than about 1.0. Illustrative of strong acids which are not susceptible to oxidation by hydrogen peroxide are sulfuric acid, phosphoric acid, p-toluene sulfonic acid, benzene sulfonic acid, methane sulfonic acid, ethane sulfonic acid and the like. The preferred strong acid for use in the process of the invention is sulfuric acid.

As indicated above, the strong acid is employed in catalytic amount, i.e. in an amount less than equimolar with respect to the starting phenol (I). Advantageously, the strong acid is employed in amount corresponding to about 0.001 mole to about 0.1 mole per mole of starting phenol (I) and, preferably, from about 0.01 mole to about 0.03 mole per mole of starting phenol (I).

The addition of the strong acid to the mixture of starting phenol (I) and peroxide initiates a reaction which is exothermic. If desired, the reaction mixture can be subjected to cooling to absorb some or all of the exotherm. Advantageously, the temperature of the reaction mixture is controlled, by cooling if necessary, so that it does not rise significantly above about 80° C. Preferably, the temperature of the reaction mixture is maintained within the range of about 10° C. to about 40° C.

The progress of the reaction, i.e. the formation of hydroquinone in the reaction mixture, can be followed by any of the routine analytical procedures employed in the art for such purposes. Illustrative of such procedures are infrared spectral analysis, gas chromatography and the like. When the formation of hydroquinone is adjudged complete on the basis of amount of hydrogen peroxide consumed or of any other of the above analytical procedures, the reaction mixture is allowed to cool to ambient temperature and the hydroquinone is recovered from the reaction product by procedures conventional in the art. For example, the ketone (II), together with any unreacted starting phenol (I) and with any hydroxy compound R"OH due to the use of a hydrocarbyl peroxide, can be removed from the reaction mixture by steam distillation after dilution of the reaction product with water. The desired hydroquinone is then isolated from the residue by extraction with an appropriate solvent such as ether, benzene, toluene, xylene and the like.

It is found that, using the above process of the invention, the conversion of the starting phenol (I) to hydroquinone can be accomplished in substantially quantitative yield and the hydroquinone can be isolated from the reaction product readily in a high state of purity.

In a further aspect of the present invention, the above described process is employed as one step, the final one, in a semi-continuous process for the conversion of phenol to hydroquinone. This process is illustrated schematically in relationship to a specific embodiment thereof as follows:

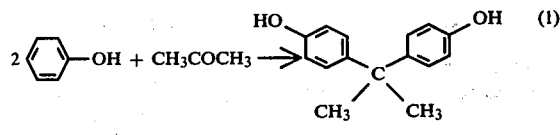 (1)

Bisphenol A

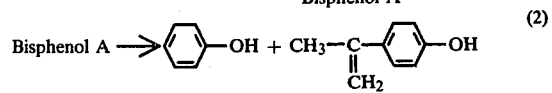 (2)

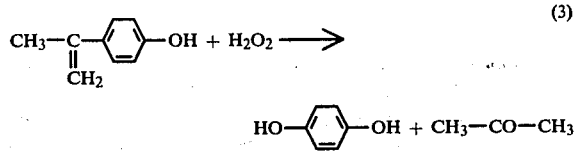 (3)

In the first stage of the above reaction scheme, phenol and acetone are condensed under conditions well known in the art to produce bisphenol A [2,2-bis(4-hydroxyphenyl)propane]; a review of the various conditions for carrying out this reaction is to be found, for example, in Angew. Chem. International Edition 2 (7) 373 (1963). Illustratively, the phenol and formaldehyde are condensed in at least substantially stoichiometric proportions, and preferably with an excess of phenol over the stoichiometric proportion, in the presence of dry hydrogen chloride. The reaction is advantageously conducted at elevated temperatures, e.g. from about 50° C. to about reflux temperature. The water eliminated in the reaction can, if desired, be removed from the reaction mixture as it is formed. The desired bisphenol A separates from solution as a solid precipitate. Any unreacted phenol can be removed from the reaction mixture, for example, by distillation or steam distillation prior to isolation of the bisphenol A by filtration.

Purification of the bisphenol A, for example, by recrystallization, reprecipitation by acidification of an alkaline solution, and the like, can be carried out, if desired, before proceeding to the next stage of the above process. However, such purification is generally unnecessary and is undesirable because it adds to the overall cost of the process.

In the second stage of the continuous process shown schematically above, the bisphenol A, with or without purification, is subjected to alkaline hydrolysis using the procedure described, for example, in British Specification 905,994. Illustratively, the bisphenol A is heated to a temperature of about 180° C. to about 230° C. in the presence of a catalytic amount of an alkali metal hydroxide such as sodium hydroxide, potassium hydroxide, lithium hydroxide and the like. The reaction is carried out under reduced pressure so that the mixture of phenol and p-isopropenylphenol which is generated is distilled from the reaction mixture as it is formed.

The amount of alkali metal hydroxide employed is catalytic, i.e. is less than 1 mole per mole of bisphenol A, and advantageously is within the range of about 0.001 mole to about 0.02 mole per mole of bisphenol A. Preferably, the amount of alkali metal hydroxide employed is within the range of about 0.005 mole to about 0.01 mole per mole.

The mixture of phenol and p-isopropenyl phenol so prepared can be separated, if desired, for example by fractional distillation, and the isopropenylphenol so isolated is then subjected to the process of the invention described above and is thereby converted to hydroquinone with the production of acetone as the by-product as shown in step (3) of the schematic representation above. Alternatively, and preferably, the mixture of phenol and p-isopropenylphenol obtained as described above is subjected, without separation or any further treatment, to the process of the invention whereby there is obtained a mixture of hydroquinone, acetone and the unchanged phenol generated in stage (2). This mixture is readily separated into its component parts by conventional procedures, for example by steam distillation, to remove both acetone and phenol followed by solvent extraction or like treatment of the distilland, to recover the hydroquinone therefrom.

It will be seen that the overall result of the three step procedure discussed above is to convert one of the two initial moles of phenol to hydroquinone and to recover one mole of acetone in the second and third stages respectively. The recovered phenol and acetone are then employed as part of the starting materials employed in a repeat of the cycle of operations, thereby rendering semi-continuous the process discussed above. The economic advantages of being able to carry out the above process in the manner described will be immediately obvious to one skilled in the art.

The above semi-continuous process has been described in relation to a specific embodiment, namely the condensation of phenol and acetone and the use of hydrogen peroxide in the final stage, for the sake of simplicity. However, the above semi-continuous processes can also be carried out using, in place of acetone, any of the ketones of formula R—CO—CH$_2$—R', wherein R and R' have the significance above defined. The overall result of the process is precisely the same as will be evident from the following equations:

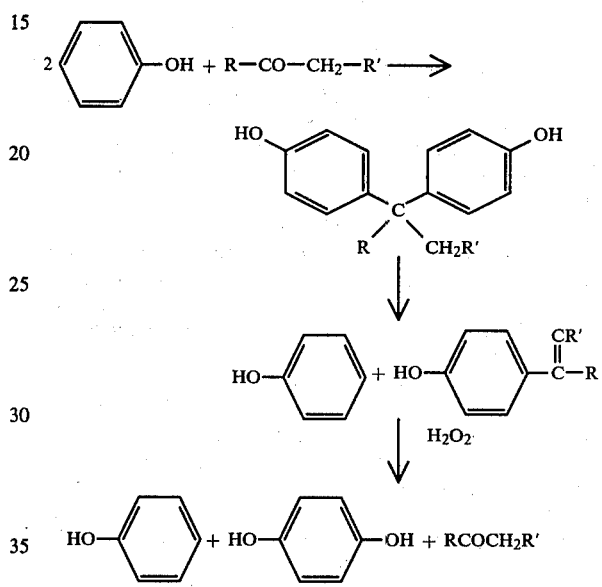

Similarly, the hydrogen peroxide employed in the final stage of the above process can be replaced by a hydrocarbyl hydroperoxide as was described in relation to the main process of the invention.

The hydrocarbyl hydroperoxides R"OOH which are employed in the process of the invention can be any of those known in the art. Illustrative of such hydrocarbyl hydroperoxides are the alkyl hydroperoxides wherein alkyl contains from 1 to 12 carbon atoms such as methyl, ethyl, propyl, butyl, pentyl, hexyl, heptyl, octyl, nonyl, decyl, undecyl, and dodecyl including isomeric forms thereof; alkenyl hydroperoxides wherein alkenyl is from 3 to 12 carbon atoms, inclusive, such as allyl, butenyl, pentenyl, hexenyl, heptenyl, octenyl, nonenyl, decenyl, undecenyl, dodecenyl, and the like including isomeric forms thereof; cycloalkyl hydroperoxides wherein cycloalkyl is from 4 to 8 carbon atoms, inclusive, such as cyclobutyl, cyclopentyl, cyclohexyl, cycloheptyl, and cyclooctyl; cycloalkenyl hydroperoxides wherein cycloalkenyl is from 4 to 8 carbon atoms, inclusive, such as cyclobutenyl, cyclopentenyl, cyclohexenyl, cycloheptenyl, cyclooctenyl, and isomeric forms thereof; and aralkyl hydroperoxides wherein aralkyl is from 7 to 13 carbon atoms, inclusive, including benzyl, cumyl (α,α-dimethylbenzyl), phenethyl, α,α-diethylbenzyl, benzhydryl, α-naphthylmethyl and the like.

Preferably, the hydrocarbyl hydroperoxides R"OOH which are employed in the process of the invention are those in which the peroxy group is attached to a tertiary carbon atom and more particularly those hydroperoxides having the structure:

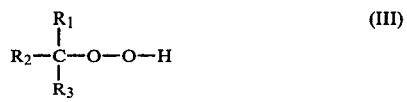
(III)

wherein $R_1$, $R_2$, and $R_3$ taken individually each represent alkyl as hereinbefore defined or aryl from 6 to 12 carbon atoms, inclusive and $R_1$ and $R_2$ taken together with the C atom to which they are attached represent cycloalkyl as hereinbefore defined. Illustrative of aryl are phenyl, tolyl, xylyl, biphenylyl, naphthyl, and the like.

Illustrative of tertiary hydroperoxides having the above formula (III) are t-butyl hydroperoxide, phenylcyclohexane hydroperoxide, triphenylmethyl hydroperoxide, cumene hydroperoxide, o-, m-, and p-isopropylbenzene hydroperoxides, 1,3,5--triisopropylbenzene hydroperoxide, 1-methylcyclohexane hydroperoxide and the like.

The above hydroperoxides are generally obtained by hydroperoxidation of the corresponding hydrocarbon using procedures well known in the art; see, for example, Hawkins, Organic Peroxides, Van Nostrand, New York, 1961. As indicated previously, the hydrocarbyl hydroperoxides can be used in purified form in the process of the invention or can be used in the form of the unpurified reaction mixture resulting from the hydroperoxidation of the parent hydrocarbon.

The p-substituted phenols (I) which are employed as starting materials in the main process of the invention are, for the most part, known compounds and can be prepared by conventional procedures. For example, they can be prepared, using the various procedures described above, by condensation of phenol with the appropriate ketone $R-CO-CH_2-R'$, wherein R and R' are as hereinbefore defined, to yield the corresponding bisphenol followed by alkaline cleavage of the latter.

The ketones $R-CO-CH_2-R'$ wherein R and R' have the significance hereinbefore defined which are employed as starting materials in the first stage of the semi-continuous process of the invention are, for the most part, known in the art and can be prepared by conventional procedures for the preparation of ketones; see, for example, Chemistry of Carbon Compounds, Ed. E. H. Rodd, Vol. IA, pages 505 to 510, 1951, Elsevier, New York.

The following examples describe the manner and process of making and using the invention and set forth the best mode contemplated by the inventor of carrying out the process of the invention but are not to be construed as limiting.

EXAMPLE 1

A solution of 2.44 g (0.0135 mole; purity 74.8 percent by weight, remainder of said material being dimer and other oligomers, said material having been prepared as described below) of p-isopropenylphenol in 20 ml of glacial acetic acid was stirred while 1.81 ml (0.018 mole) of 30 percent aqueous hydrogen peroxide was added in one portion. The resulting mixture was stirred and cooled to approximately 8° C. and 0.05 g (0.0005 mole) of concentrated sulfuric acid was added. An exothermic reaction ensued and no attempt was made to control the temperature. The maximum temperature attained was 40° C. The resulting black mixture was allowed to cool to 25° C. and was then poured into 100 ml of water. The aqueous mixture was extracted with six portions, each of 50 l ml of ether, and the ethereal extracts containing acetone were combined and dried over anhydrous magnesium sulfate. The dried solution was filtered and the filtrate was evaporated to dryness. The residue was washed with chloroform and then dried in vacuo to give 1.61 g of hydroquinone in the form of a light tan solid having a melting point of 161° to 168° C. This material was determined by infrared spectral analysis to have a purity of 93.3 percent representing an overall yield of hydroquinone, based on p-isopropenylphenol in the starting material, of 100 percent of the theoretical. The product was recrystallized from benzene to give pure hydroquinone having a melting point of 168° to 169° C.

The p-isopropenylphenol employed as starting material in the above reaction was obtained as follows:

A mixture of 165 g (0.724 mole) of bisphenol A [2,2-bis(4-hydroxyphenyl)propane], 1 g of antioxidant [1,3,5-tris(3,5-di-t-butyl-4-hydroxyphenyl)mesitylene] and 0.22 g (0.0055 mole) of sodium hydroxide was heated in a flask fitted with distillation head at 215° to 230° C. at a pressure of about 8 mm of mercury. The distillate (151 g) was collected in a flask containing 1 g of the above antioxidant and was subsequently fractionally distilled to obtain 60.1 g (88.2 percent theoretical yield) of phenol as the fraction boiling at 67° to 83° C. at 10 mm of mercury and 52.4 g (53.8 percent theoretical yield) of p-isopropenylphenol. The latter was found by gel permeation chromatography to contain 74.8 percent monomer, 9.7 percent dimer and 15.4 percent higher oligomers. It was stored under nitrogen at 0° C. before being used in further reactions.

EXAMPLE 2

This example demonstrates that p-isopropenylphenol can be oxidized to hydroquinone and acetone in the presence of phenol which latter is recovered unchanged.

A solution of 3.2 g (0.018 mole) of p-isopropenylphenol (74.8 percent purity; prepared as described in EXAMPLE 1) and 1.71 g (0.018 mole) of phenol in 20 ml of glacial acetic acid was admixed with 1.82 ml (0.018 mole) of 30 percent aqueous hydrogen peroxide. The resulting mixture was cooled to 8° C. with stirring and 0.02 ml of concentrated sulfuric acid was added. An exothermic reaction ensued. No external cooling was applied and the temperature rose to a maximum of 65° C. after 2.5 minutes. The reaction mixture was allowed to cool to room temperature before being diluted with water and extracted with six portions, each of 50 ml, of ether. The ethereal extracts, containing acetone, hydroquinone and phenol, were combined and dried over anhydrous magnesium sulfate and evaporated to dryness. The residue (3.2 g) was shown by gel permeation chromatography to contain 61.6 percent by weight of hydroquinone (representing 100 percent theoretical yield based on p-isopropenylphenyl), and 21.5 percent by weight of phenol.

In a repeat of the above experiment, the reaction mixture remaining after the exotherm had subsided was subjected directly to steam distillation to give a distillate containing phenol and acetone. The residue from the steam distillation was neutralized to pH 6 to 7 with 10 percent aqueous sodium hydroxide solution and extracted with ether. The ethereal extract was dried over anhydrous magnesium sulfate, filtered, and the filtrate evaporated to dryness to yield hydroquinone.

EXAMPLE 3

This example illustrates a semi-continuous process for the conversion of phenol to hydroquinone.

A mixture of 196.5 g (2.09 mole) of phenol and 30.1 g (0.52 mole) of acetone was stirred mechanically at 50° C. in a 3-necked flask fitted with gas inlet tube, reflux condenser, drying tube and acid scrubber while a steady stream of dry hydrogen chloride gas was bubbled through the mixture. The procedure was continued for 3.5 hours at the end of which time a total of 7.7 g (0.215 mole) of hydrogen chloride had been absorbed. The resulting mixture was cooled, neutralized to about pH 5 by the addition of 0.215 mole of 10 percent aqueous sodium hydroxide solution and subjected to steam distillation to remove excess phenol. Approximately 95 g of phenol was recovered from the distillate by extraction with ether. The residue from the distillation was cooled to approximately 25° C., and the solid which separated was isolated by filtration, washed with 100 ml of toluene and dried to obtain 114 g (96 percent theoretical yield) of bisphenol A having a melting point of 154° to 156° C.

The bisphenol A so obtained (114 g) was admixed with 1 g of antioxidant [1,3,5-tris(3,5-di-t-butyl-4-hydroxyphenyl)mesitylene] and 0.2 g of sodium hydroxide and the mixture was heated in a flask fitted with a distillation head at 215° to 230° C. at a pressure of about 8 mm of mercury. The distillate collected was a mixture of phenol and p-isopropenylphenol. This mixture was subjected without further treatment to oxidation using the procedure used in EXAMPLE 1 for the oxidation of p-isopropenylphenol to hydroquinone. The crude reaction mixture after dilution with water was subjected to distillation on a steam bath to recover the acetone present in said mixture. The residue was subjected to steam distillation to remove the phenol present in the reaction mixture. Finally, the hydroquinone was isolated from the residue by neutralization to pH 6 to 7 with aqueous sodium hydroxide followed by extraction with ether. The ether extracts were dried over anhydrous magnesium sulfate and the dried extract was evaporated to dryness to yield the desired hydroquinone.

The phenol and acetone recovered in the above process were then used as part of the reactants employed in a subsequent cycle of the above process.

EXAMPLE 4

A mixture of 188 g (2 moles) of phenol, 98 g (1 mole) of cyclohexanone and 32 g of concentrated hydrochloric acid was heated at 36° C. with stirring for 72 hours. At the end of this time water (1000 ml) was added to the solid red mass and the mixture was extracted with ether (3000 ml). The ethereal extract was washed with water and dried over anhydrous magnesium sulfate. The dried extract was filtered and the filtrate was evaporated to dryness. The residue was recrystallized from monochlorobenzene to give 75.4 g (53 percent theoretical yield) of 1,1-bis(p-hydroxyphenyl)cyclohexane in the form of a crystalline solid having a melting point of 181° to 182.5° C.

A mixture of 100 g (0.373 mole) of 1,1-bis(p-hydroxyphenyl)cyclohexane and 0.5 g of sodium hydroxide pellets was heated at approximately 255° C. at a pressure of 10 mm of mercury using a flask fitted with a distillation head and a receiver cooled in an ice bath. A total of 75.95 g of distillate was collected. One half (37.9 g) of this distillate was subjected to fractional distillation to recover phenol, boiling point 69°–76° C. at 10 mm of mercury, and 22 g (68 percent theoretical yield based on bisphenol) of 1-(p-hydroxyphenyl)cyclohexene-1 in the form of a solid of melting point 120° to 121° C.

A solution of 3.17 g (0.018 mole) of 1-(p-hydroxyphenyl)cyclohexene-1 in 30 ml of glacial acetic acid was mixed with 2.1 ml of 30 percent aqueous hydrogen peroxide. To this mixture was added with stirring at 25° C., 0.02 ml of concentrated sulfuric acid. The temperature of the reaction mixture rose to 80° C. after 2.5 minutes and, after the reaction subsided, the mixture was heated at 65° to 70° C. for one hour before being cooled to approximately 25° C. and poured into water. The resulting mixture was extracted with four 100 ml portions of ether and the combined ethereal extracts were washed with water and dried over anhydrous magnesium sulfate. The dried solution was filtered and the filtrate was distilled to remove firstly ether and then cyclohexanone. The residue was 2.12 g of hydroquinone which was shown to have a purity of 60 percent by ultraviolet spectral analysis.

EXAMPLE 5

A mixture of 20 g (0.0825 mole) 2-butylidene bisphenol (Chardonnens, Helv. Chim. Acta 12, 649, 1920) and 0.08 g of sodium hydroxide was heated at 200° C. under 10 mm of mercury in a flask fitted with a distillation head but no condenser. A pale yellow liquid (18.7 g) was collected as distillate and stored over trimethylhydroquinone at 0° C. before being fractionally distilled to obtain 6.39 g of phenol as the fraction boiling at 74° to 78° C. at 12 mm of mercury and 9.3 g of 2-p-hydroxyphenylbutene-2 having a boiling point of 131° to 136° C. at 12 mm of mercury.

A solution of 2.7 g (0.018 mole) of 2-p-hydroxyphenylbutene-2 (prepared as described above) in 20 ml of glacial acetic acid was stirred while 1.62 ml (0.027 mole) of 50 percent aqueous hydrogen peroxide was added in 1 portion. The resulting mixture was stirred and 0.05 g (0.0005 mole) of concentrated sulfuric acid was added. An exothermic reaction ensued and no attempt was made to control the temperature. The maximum temperature attained was 86° C. The resulting mixture was allowed to cool to approximately 25° C. and then poured into water. The resulting aqueous mixture was worked up as described in Example 1 to obtain 1.95 g of hydroquinone having a purity of 70 percent (as shown by ultraviolet spectral analysis). This represents a yield of 68 percent theoretical based on 2-p-hydroxyphenylbutene-2.

EXAMPLE 6

A solution of 3.25 g of p-isopropenylphenol (75 percent pure: prepared as described in Example 1; 0.014 mole) in 10 ml of anhydrous diethylether was maintained at 0° C. and treated with 0.85 ml (0.018 mole) of 50 percent aqueous hydrogen peroxide. To the resulting mixture was added 0.1 ml of concentrated sulfuric acid and then, after allowing the mixture to stand for 40 minutes, a second portion of concentrated sulfuric acid. The resulting product separated into two phases but the addition of 3 ml of glacial acetic acid caused the reformation of a single phase. The resulting product was extracted with ether, and the ethereal extract was dried over anhydrous magnesium sulfate and evaporated to dryness. There was thus obtained 1.72 g of crude hydroquinone which was shown by ultraviolet spectroscopy to have a purity of 57 percent.

EXAMPLE 7

A solution of 3.2 g (0.018 mole) of p-isopropenylphenol (75 percent pure: prepared as described in Example 1) in 34 ml of diethylether was cooled to 5° C. and 1.4 ml (0.014 mole) of 30 percent aqueous hydrogen peroxide was added. To the resulting mixture was added dropwise, with stirring, over a period of 45 minutes, a total of 13.1 ml of concentrated sulfuric acid. The temperature of the reaction mixture rose to 30° C. After the temperature of the reaction mixture had cooled to about 25° C., the resulting product was treated with 250 ml of water and the mixture was extracted with six portions each of 50 ml of ether. The ethereal extracts were dried over anhydrous magnesium sulfate and then evaporated to dryness. The residue (2.6 g) was crude hydroquinone which was shown by ultraviolet spectroscopy to have a purity of 52 percent, representing a theoretical yield of 73 percent based on starting phenol.

EXAMPLE 8

To a slurry of 2.26 g (0.016 mole) of p-isopropenylphenol (95 percent pure) in 20 ml of water at 25° C. was added dropwise, with stirring, 1.82 ml (0.018 mole) of 30 percent aqueous hydrogen peroxide. A total of 0.3 g of concentrated sulfuric acid was then added dropwise with stirring and the slurry was allowed to stand at circa 25° C. for 16 hours. At the end of this time the mixture was heated at 60° C. for 4 hours before being diluted with 200 ml of water. The resulting mixture was extracted with ether and the ethereal extract was dried over anhydrous magnesium sulfate and evaporated to dryness. The residue (1.1 g) of crude hydroquinone was shown by ultraviolet spectroscopy to have a purity of 77 percent represent an overall yield of 50 percent based on starting phenol.

EXAMPLE 9

A solution of 2.44 g (0.014 mole; 78 percent pure) of p-isopropenylphenol in 20 ml of glacial acetic acid and one drop of concentrated sulfuric acid was cooled in ice water and 1.24 g (0.018 mole) of t-butyl hydroperoxide was added dropwise with stirring over a period of 10 minutes. The temperature of the reaction mixture rose to 30° C. When the temperature had subsided, the mixture was diluted with water and extracted with ether. The ethereal extract was dried over anhydrous magnesium sulfate and the dried solution was evaporated to dryness. There was thus obtained 0.5 g of crude hydroquinone.

I claim:

1. A process which comprises reacting p-isopropenylphenol with an at least equimolar amount of hydrogen peroxide in the presence of glacial acetic acid and a catalytic amount of a strong acid selected from the group consisting of sulfuric, phosphoric, p-toluenesulfonic, benzenesulfonic, methanesulfonic and ethanesulfonic acids, said reaction being carried out at a temperature not greater than 80° C. whereby there is obtained hydroquinone and acetone.

2. The process of claim 1 wherein the strong acid is sulfuric acid.

3. The process of claim 1 wherein the p-isopropenylphenol starting material employed is a mixture thereof with phenol, said mixture having been obtained by the alkaline cleavage of bisphenol A.

4. A semicontinuous process for the conversion of phenol to hydroquinone which comprises condensing phenol and acetone in the presence of acid to obtain Bisphenol A, subjecting said Bisphenol A to alkaline hydrolysis to yield a mixture of phenol and p-isopropenylphenol subjecting said mixture of phenol and p-isopropenylphenol, without separation, to reaction with at least an equimolar amount, based on p-isopropenylphenol, of hydrogen peroxide in the presence of an inert solvent and a catalytic amount of a strong acid selected from the group consisting of sulfuric, phosphoric, p-toluenesulfonic, benzenesulfonic, methanesulfonic and ethanesulfonic acids said reaction being carried out at a temperature not greater than 80° C., to obtain a mixture of hydroquinone, phenol, and acetone, recovering the hydroquinone therefrom, and recovering the phenol and acetone generated as by-products for re-use as starting materials in a subsequent cycle of the above steps.

5. The process of claim 4 wherein the strong acid employed in the final stage is sulfuric acid.

6. A process which comprises adding a strong acid, selected from the group consisting of sulfuric, phosphoric, p-toluenesulfonic, benzenesulfonic, methanesulfonic and ethanesulfonic acids, to a mixture in solution in glacial acetic acid of p-isopropenylphenol and an at least equimolar amount, based on said phenol, of hydrogen peroxide, maintaining the temperature of the reaction mixture below about 80° C. until oxidation is substantially complete and recovering hydroquinone therefrom.

7. The process of claim 6 wherein the p-isopropenylphenol is employed in admixture with phenol in the form of the reaction product obtained by alkaline cleavage of Bisphenol A.

* * * * *

UNITED STATES PATENT AND TRADEMARK OFFICE
CERTIFICATE OF CORRECTION

PATENT NO. : 4,207,265
DATED : June 10, 1980
INVENTOR(S) : Peter S. Carleton

It is certified that error appears in the above—identified patent and that said Letters Patent is hereby corrected as shown below:

Column 8, line 4, "50 1" should read -- 50 --.

Signed and Sealed this

Twentieth Day of January 1981

[SEAL]

Attest:

RENE D. TEGTMEYER

Attesting Officer     Acting Commissioner of Patents and Trademarks